United States Patent
Wang

(10) Patent No.: US 10,201,420 B2
(45) Date of Patent: *Feb. 12, 2019

(54) PREPARATION METHODS FOR TRANSCATHETER HEART VALVE DELIVERY SYSTEMS

(71) Applicant: St. Jude Medical, Cardiology Division, Inc., St. Paul, MN (US)

(72) Inventor: Huisun Wang, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 249 days.

This patent is subject to a terminal disclaimer.

(21) Appl. No.: 15/142,613

(22) Filed: Apr. 29, 2016

(65) Prior Publication Data

US 2016/0242907 A1  Aug. 25, 2016

Related U.S. Application Data

(60) Continuation of application No. 14/215,749, filed on Mar. 17, 2014, now Pat. No. 9,326,855, which is a
(Continued)

(51) Int. Cl.
*A61F 2/24* (2006.01)
*A61F 2/962* (2013.01)
(Continued)

(52) U.S. Cl.
CPC .......... *A61F 2/2436* (2013.01); *A61F 2/2427* (2013.01); *A61F 2/962* (2013.01);
(Continued)

(58) Field of Classification Search
CPC ...... A61F 2/2427; A61F 2/243; A61F 2/2433; A61F 2/2436; A61F 2/95; A61F 2/962; A61F 2/966
See application file for complete search history.

(56) References Cited

U.S. PATENT DOCUMENTS

| | | |
|---|---|---|
| 2002/0103525 A1 | 8/2002 | Cummings |
| 2003/0109886 A1 | 6/2003 | Keegan et al. |

(Continued)

FOREIGN PATENT DOCUMENTS

| | | |
|---|---|---|
| EP | 1464303 A2 | 10/2004 |
| JP | 2008508937 A | 3/2008 |

(Continued)

OTHER PUBLICATIONS

International Search Report for Application No. PCT/US2011/001600 dated Apr. 27, 2012.
(Continued)

*Primary Examiner* — Robert Lynch
(74) *Attorney, Agent, or Firm* — Lerner, David, Littenberg, Krumholz & Mentlik, LLP

(57) ABSTRACT

A delivery device for a collapsible prosthetic heart valve includes a support shaft around which a compartment is defined, an inner shaft extending through the support shaft and adapted to slide relative to the support shaft along a longitudinal axis thereof, the inner shaft having a lumen therethrough, and a distal sheath operatively connected at a distal end to the inner shaft and slidable therewith. The compartment may receive the valve in an assembled condition, and may be selectively covered and uncovered by the distal sheath. A first flow path may provide flow communication between the lumen of the inner shaft and the compartment.

14 Claims, 3 Drawing Sheets

Related U.S. Application Data division of application No. 13/234,761, filed on Sep. 16, 2011, now Pat. No. 8,721,715.

(60) Provisional application No. 61/383,982, filed on Sep. 17, 2010.

(51) Int. Cl.
*A61F 2/966* (2013.01)
*A61F 2/95* (2013.01)

(52) U.S. Cl.
CPC ............ *A61F 2/243* (2013.01); *A61F 2/2433* (2013.01); *A61F 2/95* (2013.01); *A61F 2/966* (2013.01)

(56) References Cited

U.S. PATENT DOCUMENTS

| | | |
|---|---|---|
| 2005/0222664 A1 | 10/2005 | Parker |
| 2006/0030923 A1 | 2/2006 | Gunderson |
| 2008/0167704 A1 | 7/2008 | Wright et al. |
| 2010/0286768 A1 | 11/2010 | Alkhatib |
| 2011/0264199 A1 | 10/2011 | Tran et al. |
| 2011/0295354 A1 | 12/2011 | Bueche et al. |

FOREIGN PATENT DOCUMENTS

| | | |
|---|---|---|
| JP | 2008521501 A | 6/2008 |
| JP | 2009520535 A | 5/2009 |
| WO | 2006020028 A1 | 2/2006 |
| WO | 2007071436 A2 | 6/2007 |
| WO | 2008138584 A1 | 11/2008 |
| WO | 2009091509 A1 | 7/2009 |
| WO | 2011102968 A1 | 8/2011 |

OTHER PUBLICATIONS

International Written Opinion for Application No. PCT/US2011/001600 dated Apr. 27, 2012.
U.S. Appl. No. 61/364,453, filed Jul. 15, 2010.
U.S. Appl. No. 61/383,982, filed Sep. 17, 2010.

PREPARATION METHODS FOR TRANSCATHETER HEART VALVE DELIVERY SYSTEMS

CROSS-REFERENCE TO RELATED APPLICATION

The present application is a continuation of U.S. patent application Ser. No. 14/215,749, filed Mar. 17, 2014, which is a divisional of U.S. patent application Ser. No. 13/234,761, filed Sep. 16, 2011, now U.S. Pat. No. 8,721,715, which claims the benefit of U.S. Provisional Patent Application Ser. No. 61/383,982, filed Sep. 17, 2010, entitled "Improved Preparation Methods for Transcatheter Heart Valve Delivery Systems," the disclosures of which are hereby incorporated herein by reference.

BACKGROUND OF THE INVENTION

The present invention is related to prosthetic heart valve replacement, and more particularly to devices, systems, and methods for transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valves structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically begins to expand as the sheath covering the valve is withdrawn. Once a self-expanding valve has been fully deployed, it expands to a diameter larger than that of the sheath that previously retained the valve in the collapsed condition.

Despite the various improvements that have been made to the collapsible prosthetic heart valve delivery process, conventional delivery devices, systems, and methods suffer from some shortcomings. There therefore is a need for further improvements to the devices, systems, and methods for transcatheter delivery of collapsible prosthetic heart valves.

BRIEF SUMMARY OF THE INVENTION

A delivery device for a collapsible prosthetic heart valve, a delivery system for a collapsible prosthetic heart valve, and a method of flushing a delivery device for a collapsible prosthetic heart valve are disclosed.

A delivery device for a collapsible prosthetic heart valve includes a support shaft around which a compartment is defined, the compartment being adapted to receive the valve in an assembled condition, an inner shaft extending through the support shaft and adapted to slide relative to the support shaft along a longitudinal axis thereof, the inner shaft having a lumen therethrough, a distal sheath operatively connected at a distal end to the inner shaft and slidable therewith, the distal sheath being adapted to selectively cover and uncover the compartment and the valve, and a first flow path providing flow communication between the lumen of the inner shaft and the compartment.

The delivery device may also include a distal tip operatively connected to a distal end of the inner shaft, a distal retainer interposed between the distal tip and the compartment, and a pocket defined between the distal retainer and the distal tip. The delivery device may also include a second flow path providing flow communication between the pocket and the compartment. The second flow path may include at least one through-hole in the distal retainer. The first flow path may include an aperture in a wall of the inner shaft providing flow communication between the lumen of the inner shaft and the pocket. The delivery device may also include an insert disposed in the pocket and defining an empty space between the insert and the distal tip, the empty space being in flow communication with the lumen of the inner shaft, the insert including one or more liquid passages extending between the empty space and the pocket. The delivery device may also include a proximal retainer located at a proximal end of the compartment, and a cylindrical gap defined between a free end of the distal sheath and the proximal retainer.

A delivery device for a collapsible prosthetic heart valve includes a support shaft around which a compartment is defined, the compartment being adapted to receive the valve in an assembled condition, an inner shaft extending through the support shaft and adapted to slide relative to the support shaft along a longitudinal axis thereof, the inner shaft having a lumen therethrough, a distal sheath having a distal end operatively connected to the inner shaft and slidable therewith, the distal sheath being adapted to selectively cover and uncover the compartment and the valve, and a distal tip operatively connected to a distal end of the inner shaft, the distal tip having a passage therein providing flow communication between an exterior of the delivery device and the compartment. The passage may be adapted to self-seal such that liquid can not flow therethrough from the compartment to the exterior of the delivery device.

A delivery system for a collapsible prosthetic heart valve includes a support shaft around which a compartment is defined, the compartment being adapted to receive the valve in an assembled condition, an inner shaft extending through the support shaft and adapted to slide relative to the support shaft along a longitudinal axis thereof, the inner shaft having a lumen therethrough in flow communication with an exterior of the delivery device, a distal sheath operatively connected at a distal end to the inner shaft and slidable therewith, the distal sheath being adapted to selectively cover and uncover the compartment and the valve, a first flow path providing flow communication between the lumen of the inner shaft and the compartment, and a removable plug adapted for connection to the delivery device to occlude the flow communication between the lumen of the inner shaft and the exterior of the delivery device.

The delivery system may also include a removable cap adapted for connection to a proximal end of the inner shaft to create a liquid-tight seal at the proximal end of the inner shaft. The delivery system may also include a distal tip operatively connected to a distal end of the inner shaft, and a flushing needle having a hollow needle shaft adapted to supply a flushing liquid to the compartment through the distal tip. The delivery system may also include a distal tip operatively connected to a distal end of the inner shaft, a distal retainer interposed between the distal tip and the compartment, and a pocket defined between the distal retainer and the distal tip. The delivery system may also include a second flow path providing flow communication between the pocket and the compartment. The second flow path may include at least one through-hole in the distal retainer. The first flow path may include an aperture in a wall of the inner shaft providing flow communication between the lumen of the inner shaft and the pocket. The delivery device may also include an insert disposed in the pocket and defining an empty space between the insert and the distal tip, the empty space being in flow communication with the lumen of the inner shaft, the insert including one or more liquid passages extending between the empty space and the pocket.

A method of flushing a delivery device for a collapsible prosthetic heart valve may include providing a delivery device including a support shaft around which a compartment is defined, an inner shaft extending through the support shaft and adapted to slide relative to the support shaft along a longitudinal axis thereof, and a distal sheath having a distal end operatively connected to the inner shaft and a proximal end, the distal sheath being slidable with the inner shaft, mounting a collapsible prosthetic heart valve in the compartment, sliding the distal sheath to cover the compartment and the valve, and flushing a liquid through the compartment from a distal end of the compartment to a proximal end of the compartment.

The flushing step may include flowing the liquid out of the compartment through an opening at the proximal end of the distal sheath. The flushing step may include flowing the liquid through a lumen in the inner shaft in a direction from a proximal end of the inner shaft toward a distal end of the inner shaft, and flowing the liquid from the lumen of the inner shaft to the compartment. The flushing step may include flowing the liquid from the lumen of the inner shaft to the compartment through an aperture in a wall of the inner shaft. The delivery device may also include a distal tip operatively connected to the distal end of the inner shaft, a distal retainer interposed between the distal tip and the compartment, a pocket defined between the distal retainer and the distal tip, and an insert disposed in the pocket and defining an empty space between the insert and the distal tip. The flushing step may include flowing the liquid from the lumen of the inner shaft to the empty space, from the empty space through the insert to the pocket, and from the pocket through the distal retainer to the compartment. The flushing step may include flowing the liquid through a lumen in the inner shaft in a direction from a distal end of the inner shaft toward a proximal end of the inner shaft, and flowing the liquid from the lumen of the inner shaft to the compartment. The delivery device may also include a distal tip operatively connected to a distal end of the inner shaft, the distal tip having a passage therein. The flushing step may include flowing the liquid through the passage into the distal end of the compartment.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

DETAILED DESCRIPTION

As used herein, the terms "proximal" and "distal" are to be taken as relative to a user (e.g., a surgeon or an interventional cardiologist) using the disclosed delivery devices. "Proximal" is to be understood as relatively close to the user and "distal" is to be understood as relatively farther away from the user.

Figure 1:
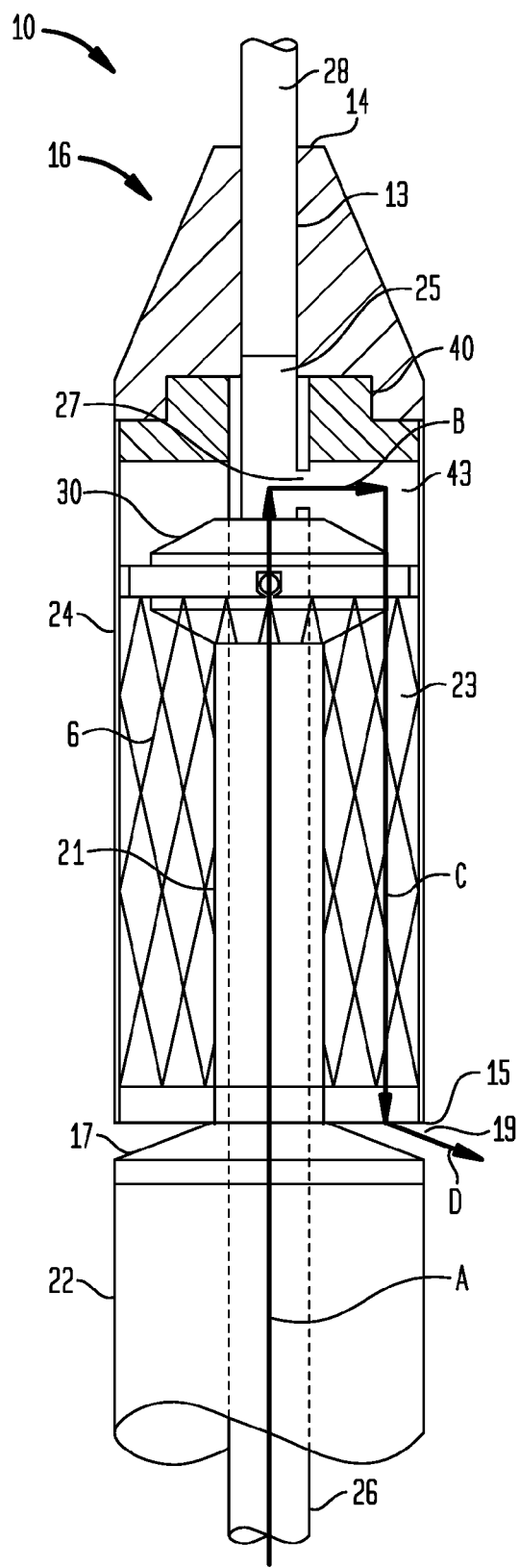
FIG. 1 is a highly schematic side elevational view of a transapical delivery device for a collapsible prosthetic heart valve according to an embodiment of the invention, shown in partial cross-section and illustrating an exemplary flow of flushing liquid through the device.

Referring to FIG. 1, an exemplary transapical delivery device 10 for a collapsible prosthetic heart valve 6 extends from a proximal end (not shown) to a distal tip 14 and includes a catheter assembly 16 for delivering the heart valve to and deploying the heart valve at a target location. The catheter assembly 16 is adapted to receive the collapsible prosthetic heart valve 6 in an assembled condition in a compartment 23 defined around a support shaft 21. A distal sheath 24 is operable for sliding movement between a closed position covering the prosthetic heart valve 6 and maintaining it in a collapsed condition, and an open position for deployment of the valve.

The support shaft 21 extends between a pair of spaced retainers 17 and 30 affixed thereto and defining the ends of the compartment 23. The retainer 30 is adapted to hold the aortic end of the prosthetic heart valve 6. The delivery device further includes an outer shaft 22, the distal end of which is connected to the retainer 17, and the proximal end of which can optionally be connected to a hub (not shown) that can be held by a user when sliding the distal sheath 24 relative to the support shaft 21.

Figure 3:
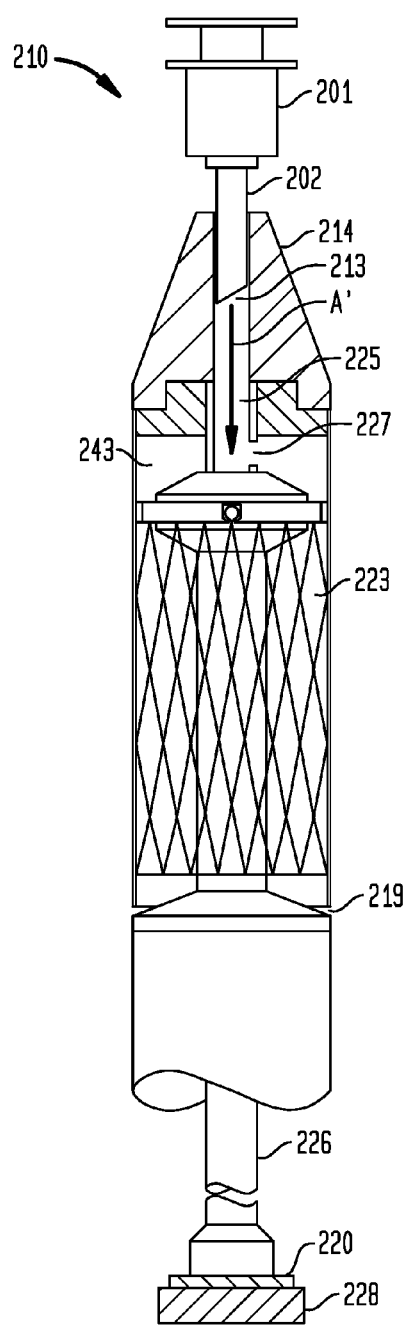
FIG. 3 is a highly schematic side elevational view of a transapical delivery device for a collapsible prosthetic heart valve according to another embodiment of the present invention, shown in partial cross-section with a flushing needle.

An inner shaft 26 extends from the proximal end of the delivery device through the outer shaft 22 and the support shaft 21 for connection to the distal tip 14. The inner shaft 26 has a lumen 25 for receiving a guide wire (not shown) therethrough. An aperture 27 is formed in the sidewall of the inner shaft 26 distally of the retainer 30 so as to provide fluid communication between the lumen 25 and a pocket 43 defined between the retainer 30 and an insert 40 affixed to the distal tip 14. The inner shaft 26 may optionally be connected to a hub that includes a luer lock coupling, e.g., as shown in FIG. 3.

The distal tip 14 has a guide wire lumen 13 that is axially aligned with the lumen 25 of the inner shaft 26. A removable plug 28 may be disposed in the distal end of the lumen 13 for creating a liquid-tight seal at the distal end of the distal tip 14. For example, the plug 28 may be made of a solid metal having an outer diameter that is about the same as or slightly larger than the inner diameter of the lumen 13, thereby producing an interference fit between the plug and the lumen.

The distal sheath 24 surrounds the support shaft 21 when the distal sheath covers the compartment 23, and is slidable relative to the support shaft such that it can selectively cover or uncover the compartment. The distal sheath 24 is affixed at its distal end to the insert 40, and through it to the inner shaft 26 and the distal tip 14. The connection of the distal sheath 24 to the insert 40 thus enables the inner shaft 26 to control the movement of the distal sheath both proximally and distally. A proximal end 15 of the distal sheath 24 abuts the retainer 17 when the distal sheath fully covers the compartment 23, as shown in FIG. 1. The proximal edge 15 is spaced apart from the retainer 17 when the compartment 23 is at least partially uncovered.

To use the delivery device 10 to insert the collapsible prosthetic heart valve 6 into a patient at a desired location, the user can first load the valve into the compartment 23 by attaching the aortic end of the valve to the retainer 30, and crimping the valve to reduce its diameter such that it fits inside of the distal sheath 24. Examples of suitable retainers and methods of coupling prosthetic valves to such retainers are shown and described in the application Ser. No. 61/364,453, filed on Jul. 15, 2010, the disclosure of which is hereby incorporated by reference herein.

Next, the user can insert the catheter assembly 16 into a patient, for example, through an incision in the apex of the patient's heart, advancing the catheter assembly until the distal sheath 24 is positioned in the aortic arch of the patient. The valve 6 may then be deployed at the desired location by sliding the inner shaft 26 and the distal sheath 24 distally relative to the support shaft 21 and the valve 6 coupled thereto, so that the valve will become uncovered and can self-expand until released from the delivery device 10.

The catheter assembly 16 is adapted to be flushed with a flushing liquid such as saline, although any other appropriate liquid may be used. It is desirable to flush the compartment 23 and the pocket 43 in order to de-air (i.e., remove air pockets or air bubbles) the area in and around the prosthetic valve 6, and to flush the inner shaft 26 in order to provide lubrication for a guide wire that may be inserted through the inner shaft during advancement of the delivery device 10 to the target location.

To flush the catheter assembly 16, the user may apply a pressurized flushing liquid to the proximal end of the lumen 25 of the inner shaft 26. A proximal-to-distal pressure gradient in the lumen 25 of the inner shaft 26 causes the flushing liquid to travel distally through the lumen of the inner shaft along the path "A" shown in FIG. 1. Because the distal end of the lumen 13 of the distal tip 14 is plugged with the liquid-tight plug 28, the flushing liquid flows out of the lumen 25 of the inner shaft 26 through the aperture 27 and into the pocket 43 along the path "B".

A distal-to-proximal pressure gradient between the pocket 43 and the compartment 23 within the distal sheath 24 causes the flushing liquid to travel proximally from the pocket along the path "C" around the outer perimeter of the retainer 30 and into the compartment. The flushing liquid continues to travel proximally along the path "C" within the compartment 23 and out therefrom along the path "D" through a cylindrical gap 19 created between the proximal end 15 of the distal sheath and the retainer 17. While the flushing liquid is traveling proximally within the compartment 23, a portion of the flushing liquid flows through the prosthetic valve 6, thereby pushing entrapped air bubbles out of the prosthetic valve. Although the exemplary liquid flow path "C" is shown extending along only one side of the prosthetic valve 6, the liquid will flow proximally throughout the entirety of the compartment 23 and the valve.

The flushing liquid travels from the proximal end of the inner shaft 26, distally through the inner shaft and out aperture 27, and then proximally through the pocket 43 and the compartment 23 to the cylindrical gap 19 in a single flushing step because of a pressure gradient in the flushing liquid between the proximal end of the inner shaft and the cylindrical gap. Because there is no exposure to the environmental pressure external to the delivery device 10 along the paths A, B, C, and D until the cylindrical gap 19, a pressure above the environmental pressure can be maintained along these paths, thereby permitting the lumen 25 of the inner shaft 26, the pocket 43, and the compartment 23 to be flushed with a pressure sufficient to de-air same. Moreover, since the flushing liquid travels through the inner shaft 26, the pocket 43, and the compartment 23 in a continuous circuit through the catheter assembly 16, only a single flushing step may be required to flush the catheter assembly, rather than separate flushing steps for (i) the inner shaft and (ii) the pocket and the compartment.

Figure 2:
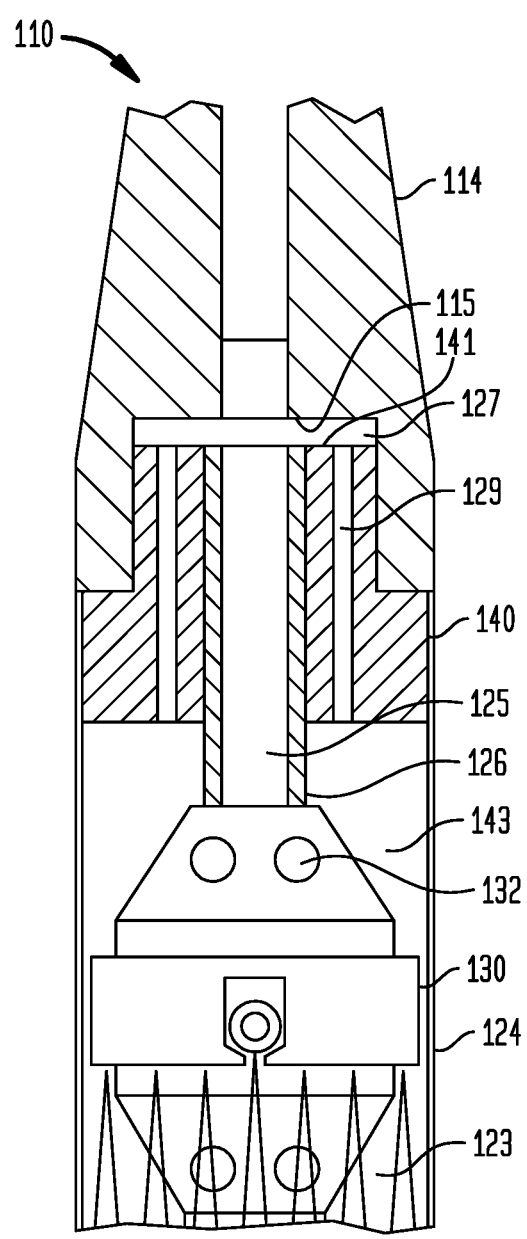
FIG. 2 is an enlarged partial cross-sectional view of a liquid communication assembly suitable for use in the delivery device of FIG. 1.

Referring now to FIG. 2, the distal end of a delivery device 110, similar to that of FIG. 1, is shown with an alternate arrangement for passing flushing liquid therethrough. In the delivery device 110, the insert 140 has a distal surface 141 that is spaced from a proximal-facing surface 115 of the distal tip 114. The distal surface 141 and the proximal-facing surface 115 define a head space 127 therebetween. A plurality of passages 129 may extend through the insert 140 and interconnect the head space 127 with the pocket 143 defined between the insert 140 and a retainer 130.

The retainer 130 may include one or more through-holes 132 that enable a flushing liquid to flow through the retainer from the pocket 143 to the compartment 123 during the flushing process. The retainer 130 may include any number and configuration of through-holes 132 that provide liquid communication between the pocket 143 and the compartment 123. The presence of the through-holes 132 in the retainer 130 enables a flushing liquid to flow proximally through the retainer, rather than flowing around the outer edges of the retainer. Such a direct route for the flushing liquid through the retainer 130 may reduce the pressure differential in the flushing liquid as the liquid traverses the retainer as compared to the pressure differential that would result from the liquid flowing between the retainer and the distal sheath 124. This difference may permit the use of a lower initial flushing liquid pressure at the proximal end of the inner shaft 126. Other than the reduced pressure differential that may be provided by the through-holes 132, the flushing operation of the delivery device 110 is similar to the flushing operation of the delivery device 10 shown and described with reference to FIG. 1.

In a variation of the embodiment shown in FIG. 2, the distal surface 141 of the insert 140 may contact the proximal-facing surface 115 of the distal tip 114, eliminating the head space 127 therebetween. In such a variant, one or more flowpaths may be established in the inner shaft 126 and the insert 140 to provide flow communication between the lumen 125 of the inner shaft and the plurality of passages 129. The flowpath may be in the form of an open reservoir extending through the entire circumference of the inner shaft 126 and through the insert 140 up to the passages 129.

Alternatively, the flowpath may be in the form of a plurality of radially projecting channels interconnecting the lumen 125 with the passages 129.

In another variation of the embodiment shown in FIG. 2, the multiplicity of passages 129 may be merged with one another to form a single passage extending through the insert 140. Such a single passage may be an annular passage that extends partially or substantially continuously around the inner shaft 126. In the variant in which a single annular passage extends substantially continuously around the inner shaft 126, one or more webs of material or other connections would preferably be provided between the portion of the insert 140 adjacent the inner shaft and the portion of the insert adjacent the distal sheath 124, so that the longitudinal movement of the inner shaft will result in a corresponding movement of the distal sheath. Such a single annular passage would provide for a greater amount of flow of the flushing liquid from the head space 127 to the pocket 143.

Referring now to FIG. 3, a delivery device 210, similar to that of FIG. 1, is shown with another alternate arrangement for passing flushing liquid therethrough. Rather than having a removable plug disposed in the distal end of the lumen of the distal tip, the delivery device 210 includes a cap 228 disposed on a hub 220 located at the proximal end of the inner shaft 226 that creates a liquid-tight seal at the proximal end of the inner shaft. With the cap 228 in place, a flushing needle 201 may be inserted into the open end of the distal tip 214 to introduce a flushing liquid into the delivery device 210. The flushing needle 201 may have a needle shaft 202 with an outer diameter that is about the same size as or slightly larger than the inner diameter of the distal end of the lumen 213 in the distal tip 214, thereby producing an interference fit between the needle shaft and the lumen.

To flush the delivery device 210, a pressurized flushing liquid is introduced into the distal end of the lumen 213 of the distal tip 214 by the flushing needle 201. A distal-to-proximal pressure gradient in the lumen 213 of the distal tip 214 causes the flushing liquid to travel proximally through the lumen of the distal tip and into and through the lumen 225 of the inner shaft 226 along the path A' shown in FIG. 3. Because the proximal end of the lumen 225 of the inner shaft 226 is capped with the liquid-tight cap 228, a buildup of pressure in the lumen causes the flushing liquid to flow out of the lumen through an aperture 227 therein and into the pocket 243. From the pocket 243, the liquid flows through the compartment 223 and the cylindrical gap 219 along substantially the same paths as paths C and D shown in FIG. 1.

When flushing the delivery device 210, the portion of the lumen 225 in the inner shaft 226 between the cap 228 and the aperture 227 is merely filled with liquid, but may not be adequately flushed. Rather, only the distalmost portion of the lumen 225 of the inner shaft 226 may be flushed along the proximal path A' taken by the flushing liquid. Therefore, a user may desire to perform a second separate flushing step by plugging the distal end of the inner shaft as described above with reference to FIG. 1, removing the cap 228 and flushing the inner shaft from the proximal end thereof. Alternatively, as this second flushing step is intended to flush only the lumen 225 of the inner shaft 226, the distal end of the inner shaft need not be plugged, and the flushing liquid can flow into the proximal end of the inner shaft and out from the distal end thereof. Such a second flushing step may provide additional lubrication of the inner shaft 226 such that a guide wire may be easily slid therethrough.

In the delivery devices shown in FIGS. 1-3, particular structures are shown that provide liquid communication between the interior of the inner shaft and the pocket within the distal sheath. The invention also contemplates the use of any alternative structures that provide such liquid communication. For example, any number of apertures, spaces, and/or passages may be provided in the delivery device to allow liquid communication between the lumen of the inner shaft and the pocket, and such apertures, spaces and/or passages may have any shape and may extend at any angle relative to the longitudinal axis of the inner shaft.

Figure 4:
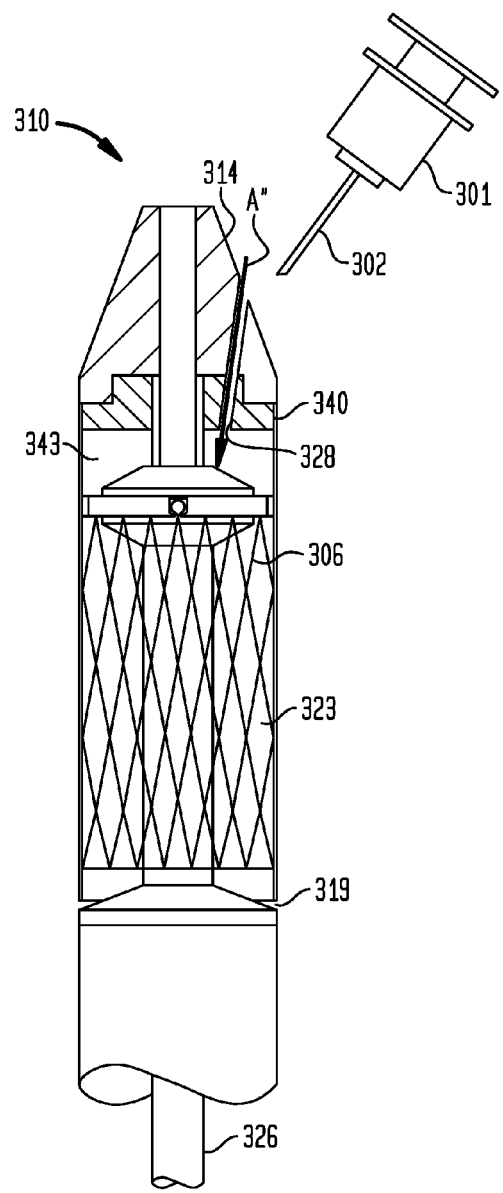
FIG. 4 is a highly schematic side elevational view of a transapical delivery device for a collapsible prosthetic heart valve according to a further embodiment of the present invention, shown in partial cross-section with a flushing needle.

Referring now to FIG. 4, a delivery device 310, similar to that of FIG. 1, is shown with yet another alternate arrangement for passing flushing liquid therethrough. The delivery device 310 has a passage 328 that extends from the pocket 343 through the insert 340 and the distal tip 314 to the external surface of the distal tip.

A flushing needle 301 may have a needle shaft 302 with an outer diameter that is about the same size as or slightly larger than the diameter of the passage 328 extending through the distal tip 314, thereby producing an interference fit between the needle shaft and the passage. Preferably, the distal tip 314 is made from a soft material such as polyether block amide (Pebax®), such that the passage 328 can self-seal upon withdrawal of the needle shaft 302 to a sufficient degree that the liquid contained in the pocket 343 will not flow out through the passage during typical use of the delivery device 310 to deliver the valve 306 into a patient.

To flush the delivery device 310, a pressurized flushing liquid is introduced into the passage 328 by the flushing needle 301. A distal-to-proximal pressure gradient in the passage 328 causes the flushing liquid to travel proximally through the passage and into the pocket 343 along the path A" shown in FIG. 4. From the pocket 343, the flushing liquid flows through the compartment 323 and the cylindrical gap 319 along substantially the same paths as paths C and D shown in FIG. 1.

When flushing the pocket 343 and the compartment 323 of the delivery device 310, the inner shaft 326 is not flushed. Accordingly, a user may desire to perform a second separate flushing step of flushing the inner shaft 326 from the proximal end or the distal end thereof. It should be appreciated that since the inner shaft 326 is not flushed when the pocket 343 and the compartment 323 are flushed, a variant of the delivery device 310 may be provided including a solid inner shaft that does not have a lumen. In such a variant delivery device, the process of flushing the pocket 343 and the compartment 323 would be the same as that described above.

The invention also contemplates the use of any alternative structures that provide liquid communication between the external environment and the pocket within the distal sheath. For example, an aperture or one or more passages may be provided in one or more of the distal tip 314, the insert 340, and the distal sheath 324 to allow liquid communication between the external environment and the pocket, and such aperture and/or passages may have any shape and may extend at any angle relative to the longitudinal axis of the inner shaft.

Although the various delivery devices have been described here in connection with deployment of a prosthetic valve having a collapsible stent structure, all of the delivery devices may be used for other purposes. In particular, the various delivery devices may be used to retain and deliver conventional collapsible stents that do not contain a valve.

Although the invention herein has been described with reference to particular embodiments in which the annulus end of a prosthetic valve is deployed first, it is to be understood that the invention contemplates embodiments in which the aortic end of a valve is deployed first. In such embodiments, the annulus end of the stent portion of the valve may be engaged with a retainer, while the aortic end of the stent may be remote from the retainer and may be unsheathed first.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery device for a collapsible prosthetic heart valve, the delivery device comprising:
   a support shaft around which a compartment is defined, the compartment being adapted to receive the valve in an assembled condition;
   an inner shaft extending through the support shaft and adapted to slide relative to the support shaft along a longitudinal axis thereof, the inner shaft having a lumen therethrough;
   a distal tip operatively connected to a distal end of the inner shaft;
   a distal retainer interposed between the distal tip and the compartment;
   a distal sheath operatively connected at a distal end to the inner shaft and slidable therewith, the distal sheath being adapted to selectively cover and uncover the compartment and the valve; and
   a first flow path providing flow communication between the lumen of the inner shaft and the compartment at a location between the distal retainer and the distal tip.

2. The delivery device of claim 1, further comprising:
   a pocket defined between the distal retainer and the distal tip.

3. The delivery device of claim 2, further comprising a second flow path providing flow communication between the pocket and the compartment.

4. The delivery device of claim 3, wherein the second flow path includes at least one through-hole in the distal retainer.

5. The delivery device of claim 2, further comprising an insert disposed in the pocket and defining an empty space between the insert and the distal tip, the empty space being in flow communication with the lumen of the inner shaft, the insert including one or more liquid passages extending between the empty space and the pocket.

6. The delivery device of claim 1, further comprising:
   a proximal retainer located at a proximal end of the compartment; and
   a cylindrical gap defined between a free end of the distal sheath and the proximal retainer.

7. A delivery system for a collapsible prosthetic heart valve, the delivery system comprising:
   a support shaft around which a compartment is defined, the compartment being adapted to receive the valve in an assembled condition;
   an inner shaft extending through the support shaft and adapted to slide relative to the support shaft along a longitudinal axis thereof, the inner shaft having a lumen therethrough in flow communication with an exterior of the delivery device;
   a distal tip operatively connected to a distal end of the inner shaft;
   a distal retainer interposed between the distal tip and the compartment;
   a distal sheath operatively connected at a distal end to the inner shaft and slidable therewith, the distal sheath being adapted to selectively cover and uncover the compartment and the valve;
   a first flow path providing flow communication between the lumen of the inner shaft and the compartment at a location between the distal retainer and the distal tip; and
   a removable plug adapted for connection to the delivery device to occlude the flow communication between the lumen of the inner shaft and the exterior of the delivery device.

8. The delivery system of claim 7, further comprising a removable cap adapted for connection to a proximal end of the inner shaft to create a liquid-tight seal at the proximal end of the inner shaft.

9. The delivery system of claim 7, further comprising:
   a flushing needle having a hollow needle shaft adapted to supply a flushing liquid to the compartment through the distal tip.

10. The delivery system of claim 7, further comprising:
    a pocket defined between the distal retainer and the distal tip.

11. The delivery system of claim 10, further comprising a second flow path providing flow communication between the pocket and the compartment.

12. The delivery system of claim 11, wherein the second flow path includes at least one through-hole in the distal retainer.

13. The delivery system of claim 10, wherein the first flow path includes an aperture in a wall of the inner shaft providing flow communication between the lumen of the inner shaft and the pocket.

14. The delivery system of claim 10, further comprising an insert disposed in the pocket and defining an empty space between the insert and the distal tip, the empty space being in flow communication with the lumen of the inner shaft, the insert including one or more liquid passages extending between the empty space and the pocket.

* * * * *